(12) United States Patent
Vincent et al.

(10) Patent No.: US 7,482,164 B2
(45) Date of Patent: Jan. 27, 2009

(54) RAPID SERIAL EXPERIMENTATION OF CATALYSTS AND CATALYST SYSTEMS

(75) Inventors: Matthew J. Vincent, Baytown, TX (US); Larry L. Iaccino, Seabrook, TX (US); John K. Pierce, League City, TX (US); Douglas B. King, Houston, TX (US); Toby W. Cox, Baytown, TX (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 11/827,782

(22) Filed: Jul. 13, 2007

(65) Prior Publication Data

US 2008/0014639 A1    Jan. 17, 2008

Related U.S. Application Data

(60) Provisional application No. 60/830,913, filed on Jul. 14, 2006.

(51) Int. Cl.
*G01N 31/10* (2006.01)
*B01J 8/00* (2006.01)

(52) U.S. Cl. .............................. 436/37; 422/78; 422/80; 422/129; 422/130; 422/211; 436/43; 436/155; 436/159; 436/161; 436/181

(58) Field of Classification Search ............. 422/64–67, 422/78, 80, 129, 130, 196, 211; 436/37, 436/43, 155, 161, 181
See application file for complete search history.

(56) References Cited

U.S. PATENT DOCUMENTS 3,431,077 A * 3/1969 Danforth ...................... 422/80

(Continued)

OTHER PUBLICATIONS

Wen, W. Y. et al, Industrial & Engineering Chemistry Process Design and Development 1984, 23, 627-637.*

(Continued)

*Primary Examiner*—Arlen Soderquist
(74) *Attorney, Agent, or Firm*—Robert A. Migliorini

(57) ABSTRACT

The present invention relates to a method of testing catalysts and catalyst systems via a plurality of stations in which each station can accommodate a common reactor module in order to accomplish unattended, automated, rapid serial experimentation. The method includes the steps of: providing within a purged chamber a storage station of pre-loaded catalyst reactors, a hydrocarbon reaction station, one or more additional pre-treatment and/or post-treatment stations in series with said hydrocarbon reaction station, and a robotic means for moving catalyst reactors within the purged chamber between stations, pre-treating the pre-loaded catalyst reactor with a treatment gas in the post-treatment station, reacting the pre-loaded catalyst reactor with a hydrocarbon reactant in the hydrocarbon reaction station, post-treating the pre-loaded catalyst reactor with a treatment gas in the post-treatment station, and repeating the foregoing steps such that the pre-treating, reacting and post-treating steps occur simultaneously for two different pre-loaded catalyst reactors. The advantages of the present invention include improved accuracy, reproducibility and quality of test data generated, increased testing throughput rate, providing for automated unattended operation of the device, providing for the ability the ability to program a variety of sequences and settings, providing for the combination of a variety of processes (pre-treatment, HC reaction testing, post-treatment, aging, and characterization), and providing for higher temperature operation. The method finds application in laboratory test environments, and in particular in high throughput testing environments.

44 Claims, 2 Drawing Sheets

Exemplary Schematic of Process for Testing Catalysts via Rapid Serial Experimentation

U.S. PATENT DOCUMENTS

| | | | | |
|---|---|---|---|---|
| 3,536,452 | A | * | 10/1970 | Norton et al. .................. 422/63 |
| 3,583,230 | A | * | 6/1971 | Patterson ................. 73/864.85 |
| 3,832,140 | A | * | 8/1974 | Lorch et al. .................... 422/65 |
| 4,094,923 | A | * | 6/1978 | Dixon ........................ 585/714 |
| 4,099,923 | A | | 7/1978 | Milberger |
| 4,221,568 | A | * | 9/1980 | Boettger ...................... 436/48 |
| 4,600,827 | A | * | 7/1986 | Linwood et al. ............ 219/492 |
| 4,824,790 | A | * | 4/1989 | Carangelo et al. ........... 436/157 |
| 5,866,072 | A | * | 2/1999 | Bowe et al. ................... 422/78 |
| 6,265,626 | B1 | | 7/2001 | Carr et al. |
| 6,508,984 | B1 | * | 1/2003 | Turner et al. .................. 506/12 |
| 6,627,881 | B1 | * | 9/2003 | Bertrand et al. ............. 250/288 |
| 6,827,903 | B2 | | 12/2004 | Guerra |
| 2003/0040116 | A1 | * | 2/2003 | Canos et al. ................... 436/37 |
| 2005/0031491 | A1 | | 2/2005 | Canos et al. |
| 2005/0260768 | A1 | | 11/2005 | Cawse |

OTHER PUBLICATIONS

Xanthopoulou, G., Applied Catalysis, A: General 1999, 182, 285-295.*

Jeong, S. M. et al, Catalysis Today 2002, 74, 257-264.*

Hagemeyer, A.; Strasser, P.; Volpe, A. F. (eds.), High-Throughput Screening in Chemical Catalysis (2004), p. 4-11, 68-75.

Oh, Kwang Seok; Park, Yong Ki; and Woo, Seong Ihi, "Highly Reliable 64-Channel Sequential and Parallel Tubular Reactor System for High-Throughput Screening of Heterogeneous Catalysts", Review of Scientific Instruments (2005), 76(6), 062219/1-062219/7, Coden: Rsinak; ISSN; 0034-6748 Abstract only.

Mills, Patrick L. and Nicole, Jacques F., "A Novel Reactor for High-Throughput Screening of Gas-Solid Catalyzed Reactions", Chemical Emgineering Science (2004), 59 (22-23), 5345-5354 Coden: Cescac; ISSN; 0009-2509 Abstract only.

Pantu, Piboon and Gavalas, George R., "A Multiple Microreactor System for Parallel Catalyst Preparation and Testing", AIChe Journal (2002), 48(4), 815-819 Coden: AICEAC; ISSN; 0001-1541 Abstract only.

Paffett, Mark T. and Dogruel, David, "Technological Progress and Approaches to Combinatorial Testing of Heterogeneous Catalysts", Abstracts of Papers, 221st ACS National Meeting, San Diego, CA, United States, Apr. 1-5, 2001 (2001) IEC-131 Coden: 69FZD4.

Rodemerck, U.; Ignaszewski, P.; Lucas, M.; Claus, P. and Baerns, M., "Parallel Synthesis and Fast Screening of Heterogeneous Catalysts", Topics in Catalysis (2000), 13(3), 249-252 Coden: Tocafi; ISSN: 1022-5528. Also published in Microreaction Technology: Industrial Prospects, Proceedings of the International Conference of Microreaction Technology, 3rd, Frankfurt, Apr. 18-21, 1999 (1999), 287-293. Editor(s) Ehrfeld, Wolfgang; Publisher: Springer-Verlag, Berlin, Germany, Coden: 69BCAE abstract.

* cited by examiner

Exemplary Schematic of Process for Testing Catalysts via Rapid Serial Experimentation Exemplary Schematic of Process for Testing Catalysts via Rapid Serial Experimentation

RAPID SERIAL EXPERIMENTATION OF CATALYSTS AND CATALYST SYSTEMS

CROSS-REFERENCE TO RELATED APPLICATION

This application claims the benefit of U.S. Provisional Application 60/830,913 filed Jul. 14, 2006.

FIELD OF THE INVENTION

The present invention relates to the field of catalyst testing. It more particularly relates to an improved method of testing catalysts and catalyst systems through automation. Still more particularly, the present invention relates to an improved method of testing catalysts and catalyst systems by incorporating both catalyst treatment and reaction testing and characterization into distinct stations for simultaneous experiments.

BACKGROUND OF INVENTION

High throughput catalyst testing has been often accomplished via the "massively parallel" approach discussed in High-Throughput Screening in Chemical Catalysis (2004 Wiley-VCH Verlag GmbH & Co. and KGaA, Weinheim. In this prior art, an array of materials are tested as a single batch in a manner that is highly dependent on manual operation. In this experimentation approach, each well in the array is loaded with a catalyst, sealed and then heated to a single operating temperature. Once at temperature, a reaction (typically, hydrocarbon (HC)) testing proceeds. Any characterization after reaction (i.e. BET analysis, coke content) requires a separate operation. Each catalyst from the array requires the one-by-one manual discharging, segregating, weighing and re-loading into each addition characterization device. As a whole, the sequential characterization of catalysts becomes the slow step and is no longer high-throughput. Although the testing and characterization results and operation under this prior art approach are naturally disparate, the inclusion of both is necessary to generate a complete evaluation of a catalyst.

Parallel testing of catalyst reactors has been used for materials that require long times to test. However, parallel testing such as that referenced in German Patent No. DE19809477C2 is not always effective in evaluating materials in which reaction testing and characterization techniques must be combined to present a complete analysis. For example, a significant amount of carbon is deposited on materials that are evaluated in heterogeneous reactors at high temperature. Without a sequential catalyst characterization, the amount of coke deposited on the catalyst must be calculated via carbon balance. However, this methodology is unreliable because it requires that all species be measured and be measured accurately. Missing components and propagation of error lead to highly inaccurate, scattered results. Thus, calculating coke from all of those measurements is rendered unusable.

The direct measurement of coke (likely via combustion) is not a viable solution for parallel reactor systems because the arrays of materials may have to be unloaded from the reactor into a new reactor for de-coking and tested one-by-one. Alternatively, the reactor in the parallel method may have to be transferred to another experimental set-up. Another approach is to redesign the hydrocarbon feed system to include both air and hydrocarbon feeds that are appropriately separated by interlocks (although possible, also of considerable hazard) to accomplish the coke measurement. All of these approaches become a bottleneck to high-throughput experimentation.

Parallel apparatus by nature are complex mechanisms. Compromise must be reached between data quality and complexity. As a result, parallel apparatus do not contain sufficient instrumentation to control key process parameters i.e. pressure, flow, and temperature for each individual reactor. In addition, some parameters have a limited range of operation temperature for "massively parallel." While catalyst performance can be tested for many catalysts at once, data quality suffers. This leads to high variability in measured results.

A need exists for an improved method of testing catalysts and catalyst systems to alleviate the aforementioned issues associated with the prior art technique of using the massively parallel technique.

SUMMARY OF INVENTION

It has been discovered that serial testing of catalysts and catalyst systems may be made advantageously more efficient through the use of a multi-station testing arrangement and automating the testing protocol to enable faster cycling of reactors (or short reaction times) resulting in a decrease in the cumulative time to test, characterize, and change reactors.

According to the present disclosure, an advantageous method of testing catalysts and catalyst systems via a plurality of stations, in which each station can accommodate a common reactor module in order to accomplish unattended, automated, rapid serial experimentation comprises the following steps: (a) providing within one or more purged chambers a storage station of pre-loaded catalyst reactors, a hydrocarbon reaction station, a post-treatment station in series with said hydrocarbon reaction station, and a robotic means for moving catalyst reactors within said one or more purged chambers, (b) moving with said robotic means a pre-loaded catalyst reactor from said storage station to said hydrocarbon reaction station, (c) reacting said pre-loaded catalyst reactor with a hydrocarbon reactant in said hydrocarbon reaction station under controlled time, temperature, flow rate and pressure conditions, (d) moving with said robotic means said pre-loaded catalyst reactor from said hydrocarbon reaction station to said post-treatment station, (e) post-treating said pre-loaded catalyst reactor with a treatment gas in said post-treatment station under controlled time, temperature, flow rate and pressure conditions, (f) moving with said robotic means said pre-loaded catalyst reactor from said post-treatment station to said storage station, and (g) repeating the foregoing steps such that reacting and post-treating steps occur simultaneously for two different pre-loaded catalyst reactors.

A further aspect of the present disclosure relates to an advantageous method of testing catalysts and catalyst systems via a plurality of stations, in which each station can accommodate a common reactor module in order to accomplish unattended, automated, rapid serial experimentation comprising the following steps: (a) providing within one or more purged chambers a storage station of pre-loaded catalyst reactors, a pre-treatment station, a hydrocarbon reaction station in series with said pre-treatment station, and a robotic means for moving catalyst reactors within said one or more purged chambers, (b) moving with said robotic means a pre-loaded catalyst reactor from said storage station to said pre-treatment station, (c) pre-treating said pre-loaded catalyst reactor with a treatment gas in said pre-treatment station under controlled time, temperature, flow rate and pressure conditions, (d) moving with said robotic means said pre-loaded catalyst reactor from said pre-treatment station to said hydrocarbon reaction station, (e) reacting said pre-loaded catalyst reactor with a hydrocarbon reactant in said hydrocarbon reaction station under controlled time, temperature, flow rate and pressure conditions, (f) moving with said robotic means said pre-loaded catalyst reactor from said hydrocarbon reaction station to said storage station, and (g) repeating the foregoing steps such that said pre-treating and reacting steps occur simultaneously for two different pre-loaded catalyst reactors.

Another aspect of the present disclosure relates to an advantageous method of testing catalysts and catalyst systems via a plurality of stations, in which each station can accommodate a common reactor module in order to accomplish unattended, automated, rapid serial experimentation comprising the following steps: (a) providing within one or more purged chambers a storage station of pre-loaded catalyst reactors, a pre-treatment station, a hydrocarbon reaction station in series with said pre-treatment station, a post-treatment station in series with said hydrocarbon reaction station, and a robotic means for moving catalyst reactors within said one or more purged chambers, (b) moving with said robotic means a pre-loaded catalyst reactor from said storage station to said pre-treatment station, (c) pre-treating said pre-loaded catalyst reactor with a treatment gas in said pre-treatment station under controlled time, temperature, flow rate and pressure conditions, (d) moving with said robotic means said pre-loaded catalyst reactor from said pre-treatment station to said hydrocarbon reaction station, (e) reacting said pre-loaded catalyst reactor with a hydrocarbon reactant in said hydrocarbon reaction station under controlled time, temperature, flow rate and pressure conditions, (f) moving with said robotic means said pre-loaded catalyst reactor from said hydrocarbon reaction station to said post-treatment station, (g) post-treating said pre-loaded catalyst reactor with a treatment gas in said post-treatment station under controlled time, temperature, flow rate and pressure conditions, (h) moving with said robotic means said pre-loaded catalyst reactor from said post-treatment station to said storage station, and (i) repeating the foregoing steps such that said pre-treating, reacting and post-treating steps occur simultaneously for two different pre-loaded catalyst reactors.

Numerous advantages result from the advantageous method of testing catalysts and catalyst systems via rapid serial experimentation disclosed herein and the uses/applications therefore.

For example, in exemplary embodiments of the present disclosure, the disclosed method of testing catalysts and catalyst systems via rapid serial experimentation provides for a decrease in catalyst testing times.

In a further exemplary embodiment of the present disclosure, the disclosed method of testing catalysts and catalyst systems via rapid serial experimentation provides for high reproducibility and quality of test data.

In a further exemplary embodiment of the present disclosure, the disclosed method of testing catalysts and catalyst systems via rapid serial experimentation provides for automated unattended operation of the catalyst test equipment.

In a further exemplary embodiment of the present disclosure, the disclosed method of testing catalysts and catalyst systems via rapid serial experimentation provides for the ability to program a variety of settings and sequences in automating the testing and characterization protocols (e.g. each catalyst has its own recipe that determines its order to be tested, characterized, treated, re-tested, re-characterized, re-treated and so on and so forth).

In a further exemplary embodiment of the present disclosure, the disclosed method of testing catalysts and catalyst systems via rapid serial experimentation provides for pre-treatment, reaction, post treatment and characterization steps conducted in a simultaneous manner.

In another exemplary embodiment of the present disclosure, the disclosed method of testing catalysts and catalyst systems via rapid serial experimentation provides for higher testing temperatures.

In another exemplary embodiment of the present disclosure, the disclosed method of testing catalysts and catalyst systems via rapid serial experimentation provides for the ability to characterize test results without exposing the catalyst to environmental conditions that may alter the results.

In still yet another exemplary embodiment of the present disclosure, the disclosed method of testing catalysts and catalyst systems via rapid serial experimentation provides for the ability to conduct high throughput experimentation by simultaneously evaluating more than one catalyst reactor sequentially.

In still yet another exemplary embodiment of the present disclosure, the disclosed method of pre-treatment and post-treatment of reactors in bulk enables reduced time in the reaction station, thereby increasing the rate of throughput.

In still yet another exemplary embodiment of the present disclosure, the disclosed method of testing catalysts and catalyst systems via rapid serial experimentation provides for the ability to conduct pretreatment, hydrocarbon testing, characterization, aging and post-treatment in any specified order, including reproducing several steps.

In still yet another exemplary embodiment of the present disclosure, the disclosed method of testing catalysts and catalyst systems via rapid serial experimentation provides for the development of a queue for each station (HC testing, aging etc.) in a manner in which continuous, unattended operation is enabled such that down time is minimized and throughput is optimized.

These and other advantages, features and attributes of the disclosed method of testing catalysts and catalyst systems via rapid serial experimentation of the present disclosure and their advantageous applications and/or uses will be apparent from the detailed description which follows, particularly when read in conjunction with the figures appended hereto.

DETAILED DESCRIPTION OF THE INVENTION

Figure 1:
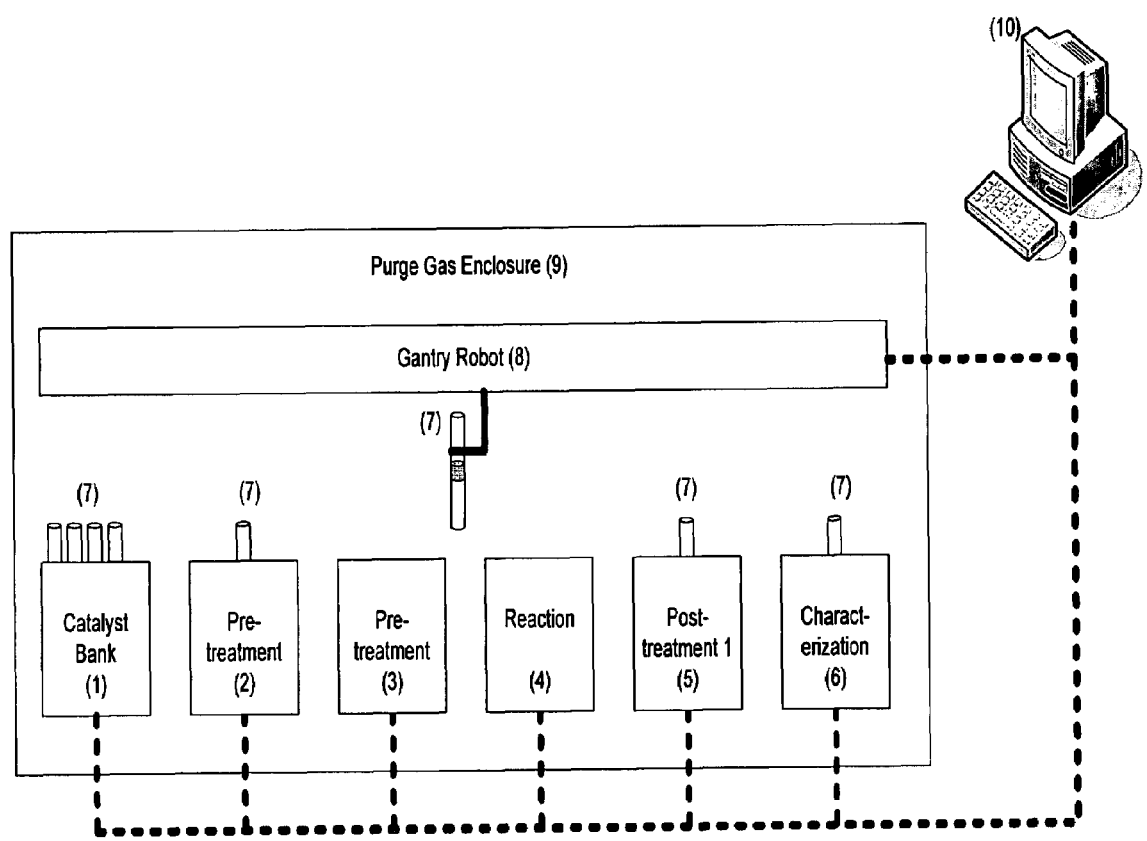
FIG. 1 depicts an exemplary schematic of a process for testing catalysts via rapid serial experimentation including storage, pre-treatment, hydrocarbon reaction, post-treatment, and characterization stations.

The present invention relates to a novel method of using serial testing as a means to rapidly test catalysts and catalyst systems. The method of using rapid serial testing as a means to test catalysts and catalyst systems is distinguishable over the prior art in providing and utilizing modular reactors designed to be transportable between a hydrocarbon testing station, and a pre-treatment, post-treatment, aging and/or characterization stations and utilizing automation to enable these catalyst containing reactors to be wholly transported between stations for serial treatment, testing and characterization purposes. The prior art methods for high throughput testing employ one testing station for simultaneously testing (also referred to as testing in parallel) more than one catalyst reactor, whereas the present invention utilizes a multiple station approach.

The present invention also discloses a method for treating pre-loaded catalyst reactors in bulk (in the pre-treatment, post-treatment and aging stations) while simultaneously testing pre-loaded catalyst reactors in a serial fashion (in the hydrocarbon reaction testing and characterization stations) to achieve reduced experimentation times. Treating in bulk is defined as simultaneously conditioning or treating more than one pre-loaded catalyst reactor in a given station and does necessarily require an active measurement of an intrinsic material property or a property of any evolving or converted products. Testing in a serial fashion is defined as testing one at a time pre-loaded catalyst reactors. "Massively" parallel refers to when approximately 24 or more pre-loaded catalyst reactors are being treated at the same time (in a parallel fashion). By decoupling the parallel treatment of one or more catalyst reactors with the serial testing of one catalyst reactor, the time to test a catalyst reactor (via reaction and characterization) is reduced to allow for more rapid serial experimentation. In addition, the use of robotics and computer controlled processing between stations and within stations permits for unattended, process automation and further minimization of the time needed to treat, react and characterize pre-loaded catalyst reactors. Furthermore, the prior art parallel approaches to catalyst reactor testing are best suited to simultaneously testing different catalyst materials under a give set of conditions, whereas the present invention is more advantageous for testing a single catalyst materials over a range of treating and testing conditions.

An alternate approach to "massively parallel" high throughput catalyst testing is via serial testing of catalysts. Due to the lack of control of key parameters in the parallel apparatus, the researcher testing catalysts and catalyst systems progresses through an experimental matrix via a serial approach. A parallel apparatus is poorly suited to rapid serial operation. The complex sealing mechanisms of parallel systems are problematic and prevent both fast and automated reactor exchanges. As a result, parallel systems require manual catalyst discharging, weighing and reloading before any other step which is both cumbersome and time consuming. When system downtime due to reactor exchange and sealing issues are included, overall throughput of the parallel system can be lower than a fast serial system.

The present invention discloses an improved method of using serial testing to rapidly evaluate catalytic systems. Exemplary catalyst types suitable for testing by the rapid serial method of the present invention include, but are not limited to, zeolites, mixed metal oxides, metal sulfides, metal nitrides, metal carbides, supported metals and their combinations. Catalyst types may be supported on metal or polymer support materials. Catalyst and catalyst supports are contained within a reactor for testing purposes. One exemplary, but non-limiting type of reactor is a quartz tube or other tubular type of reactor that is portable and easily transportable by a robotic means. Polymeric or grafitic materials may be used to provide a seal between the tubular reactors and the supply/effluent line to the reactor.

The rapid serial method of the present invention is suitable for any heterogeneous catalysis reaction, and one preferred reaction is the hydroprocessing of hydrocarbons. The catalyst in reactor of the present invention is tested in a hydrocarbon reaction station or assembly. The HC reaction station tests one reactor at a time under controlled conditions for HC reactant type, temperature, pressure, reaction time, and flow rate. Exemplary hydrocarbons for reacting catalysts include, but are not limited to, methane, higher alkanes, olefins, aromatics, alcohols, ethers, oxygenates, carbon containing compounds, hydrogen containing compounds and oxygen containing compounds.

In close proximity to the HC reaction station may be a catalyst reactor storage rack, also referred to as a catalyst reactor tray, storage station, storage tray or ante-chamber. The storage station or tray may contain any number of pre-loaded catalyst reactors in the queue for HC testing, characterization or treatments (both pre- and post-). The storage station or tray may accommodate a common reactor module. The common reactor module may be a single reactor tube or an array of reactor tubes. That is the common reactor module allows for easy interchangeability and transportability of one or more pre-loaded catalyst reactors between the various stations in the assembly. The storage station or tray may be purged with an inert gas to a predetermined pressure in preparation for HC testing, aging or characterization. In addition the storage station or tray may be heated or cooled to a predetermined temperature in preparation for HC testing, aging or characterization.

In addition to the HC reaction station, the rapid serial method of the present invention includes at least one or more additional stations or assemblies in series with the HC reaction station. One exemplary type of one or more additional stations or assemblies is a pre-treatment station for treating catalyst before the HC reaction station. For example, in a pretreatment station, fresh or spent catalysts may be dried to prevent catalyst degradation prior to HC reaction. Another exemplary type of one or more additional stations or assemblies is a post-treatment station for treating catalyst after the HC reaction station. A pre-treatment step is conducted prior to the HC reacting step, a catalyst post-treatment step is conducted after the HC reacting step. For example, in a post-treatment station, used catalyst may be oxidized in air (de-coke or passivate) to prevent autoignition. Other exemplary, pre-treatment and post treatment types include, but are not limited to, drying, passivation, oxidation, reduction, carburization, sulfidation, nitridation, and phosphoridation. In both the pre-treatment and the post-treatment stations, one or more reactors may be conditioned under controlled conditions for gas type, temperature, pressure, reaction time, and flow rate. Exemplary gases for pre-treating and post-treating catalyst reactors include, but are not limited to, hydrogen, air, oxygen, nitrogen, helium, argon, ammonia, steam, hydrogen sulfide, sulfur containing compounds, oxygen containing compound, nitrogen containing compounds, phosphorous containing compounds, carbon containing compounds and any of their combinations. These gases may also be diluted (such as with a gas previously listed) to control the rate of reaction and amount of heat released or consumed. Catalyst drying may be conducted in a heating block under an inert atmosphere for a pre-determined time and temperature prior to HC reaction testing.

Another exemplary type of at least one or more additional stations or assemblies in series with the HC reaction station or assembly is an aging station for catalyst aging. Exemplary catalyst aging treatments include, but are not limited to, thermal, hydrothermal, reduction, oxidation, carburization processes or their combination.

Another exemplary type of at least one or more additional stations or assemblies in series with the HC reaction station or assembly is a catalyst characterization station for characterizing the catalyst materials either before or after the HC reaction. Exemplary catalyst characterization methods include, but are not limited to, gas chromatography, mass spectrometry, infrared spectroscopy, chemisorption, acidity testing, adsorption, desorption, BET analysis, BJH analysis, surface area, pore volume, XRD, XRF, and ICP.

The catalyst station, HC reaction station, and at least one or more additional stations, and the robotic means for moving catalyst reactors between stations are incorporated into a purged chamber or glove box for anaerobic storage of catalysts. Exemplary purge gases include, but are not limited to, helium, hydrogen, nitrogen, argon, and mixtures thereof. The rapid serial method may be performed at high temperatures by fabricating the stations, reactors, glove box, and robotic means from materials of construction suitable for high temperature applications.

A robotic means controlled by programmable logic controller or computer is used to move catalyst reactors from station to station within the glove box. The PLC or computer may be programmed to achieve any sequence of movements of catalyst reactor between HC reaction, pre-treatment, post-treatment, aging, and characterization stations. The robotic means may be supported within the glove box by a support bridge or arm assembly. Any of a number of testing and characterization protocols may be programmed into the PLC or computer for varying the sequence of catalyst reactor movement and time at each of the stations. The computer or PLC interface may also be used to control station temperatures, test times (ramp-up, hold and ramp down), gas flow rates, and pressures. For example, flow may be controlled by changing the pressure differential across a critical orifice. In addition, the PLC may be used to open and close gas valves for sequencing different gas types through the glove box assembly. The computer or PLC interface may also be used for the acquisition and calculation of catalyst property data generated by the catalyst characterization station. The computer or PLC interface may also employ fuzzy logic. For example, fuzzy logic may be utilized to decide the start and stop times for testing a particular catalyst reactor.

In one exemplary embodiment of the present invention, the rapid serial method of the present invention includes a pre-treatment station for bulk drying, a testing station for HC reaction and a characterization station for measuring coke deposited (regeneration). The aforementioned stations are contained within a glove box with a robotic means coupled to a PLC or computer. The PLC or computer may be programmed to do only reaction testing or de-coking. The PLC or computer may also be programmed to de-coke each catalyst sample after HC reaction. Additionally, the PLC or computer may be programmed with ramp rates and hold times for de-coking. Alternatively, the PLC or computer may be programmed to alternate reaction/de-coking for a number of times for each catalyst sample, and the weight hour space velocity (WHSV) may be varied to determine the kinetics of reaction for a single sample.

In an alternative embodiment of the present invention, the rapid serial method may be provided with a third station. The third station may be another catalyst characterization station or an aging station to augment the HC reaction station and the de-coking station. In another embodiment of the present invention, the rapid serial method may be provided with a fourth station. For example, a pre-treatment station for pre-conditioning the catalyst reactor prior to HC testing. In another alternative embodiment, the rapid serial method of the present invention may be provided with five or more stations within the glove box assembly. Under each of the embodiments of the present invention utilizing two or more stations, the process is operated in a serial methodology to achieve high throughput testing. The rapid serial method of the present invention is not limited in terms of number and types of stations that may be used in conjunction with the HC reaction station. Any combination of one or more pre-treatment, post-treatment, aging and characterization stations may be utilized in a serial approach with the HC reaction station to achieve high throughput testing.

In another exemplary embodiment of the present invention, a reactor packed with catalyst is passed from station-to-station in a manner resembling an assembly line (serially). At each station, a particular operation of treatment, testing (i.e. HC), or characterization is performed. A holding tray is utilized to provide a queue for holding and selecting tubes. A purged chamber is provided to reduce exposure to air and mitigate the time required to re-condition a catalyst prior to testing, treatment or characterization. Each station contains a different reactor or set of reactors and operating parameters are controlled via a computer to organize selection, time and operating conditions. Optimized robotic operation within a purged chamber enables automated, unattended experimentation that is high-throughput.

In another exemplary embodiment of the present invention, reactors are designed in a manner to be transportable between hydrocarbon testing and de-coking set-ups with the incorporation of clever automation to enable reactors containing catalyst to be wholly transported to the de-coking set-up, where the operation is performed. In addition, reactors may be optionally transported to a system for other characterization (i.e. BET) in which the same reactor containing catalytic material is used. This method permits de-coking and/or BET characterization testing to be conducted while the next catalyst is simultaneously undergoing HC reaction.

Under the present invention, in order to accomplish serial testing in an efficient manner, two (or more) assemblies or stations are constructed. For the example above, a de-coking station and a hydrocarbon reaction station were constructed in near proximity to enable reaction of one catalyst sample in the HC reaction station with simultaneous de-coking of another catalyst sample in the catalyst de-coking station. Sample exchange between stations and reactor assemblies are automatically controlled via a robotic transport means and programmed recipes. A computer queue system may be used to track location of catalyst samples, run stored recipes (protocols), and provide unattended operation of the complete rapid serial system. A feed header may be used to manipulate gas composition for both assemblies. In addition, pressure, temperature and flow rates to each assembly or station are independently controlled.

Under the present invention, to improve the cycle time between reaction tests (or de-cokes), both assemblies or stations are contained within an inert atmosphere and queued while being maintained within a heating block. This eliminates the need for pre-drying and extensive pre-heat of the samples. Dehydrated samples advantageously enable faster ramp rates to reaction (operating) temperature and also prevent unintended oxidation of the sample between reaction and de-coking. Thus, both cycling time, and data quality is improved via sample handling. Samples are only allowed to cool for sufficient time to enable transport between reactor assembly and sample stations. Further reductions in cycle times may be realized by utilizing a moving split furnace-heater design whereby reactor tubes are transferred between stations without the need for lengthy heat-up and cool-down cycles. Heaters remain at elevated temperature set-points and move away from the reactor tubes while fans blow cool air across the reactors enable faster heat transport.

FIG. 1 is an exemplary process schematic of the method of the present invention for testing catalysts and catalyst systems via a plurality of stations in which each station can accommodate a common reactor module in order to accomplish unattended, automated, rapid serial experimentation. The figure includes the following components: a catalyst bank or storage tray or station 1, a first pre-treatment station 2, a second pre-treatment station 3, a hydrocarbon reaction station 4, a post-treatment station 5, a catalyst characterization station 6, one or more pre-loaded catalyst reactor tubes 7, an overhead gantry robot 8, a purged gas enclosure 9, and a computer or programmable logic controller 10. The gantry robot 8 moves the pre-loaded catalyst reactor tubes 7 between all of the stations 1, 2, 3, 4, 5, 6 within the confines of the purged gas enclosure 9, such that the catalyst reactor tubes 7 are moved within the process without exposure to air (anaerobic processing conditions). The catalyst bank or storage station 1 for queuing catalysts includes at least one, and preferably multiple pre-loaded catalyst reactor tubes 7. The gantry robot 8 moves reactor tubes 7 from the catalyst bank or storage station 1 to the first pretreatment station 2 for preconditioning. The gantry robot 8 also moves reactor tubes 7 from the first pretreatment station 2 to the second pretreatment station 3 for second preconditioning. Multiple catalyst reactors 7 may be simultaneously preconditioned within each of the pretreatment stations 2, 3. In one non-limiting example, the first pretreatment station 2 dries one or more catalyst reactors 7 and the second pretreatment station oxidizes the one or more catalyst reactors.

Referring to FIG. 1, following pre-treatment conditioning, the gantry robot 8 moves catalyst reactor tubes 7 from the second pre-treatment station 3 to the hydrocarbon reaction station 4 for hydrocarbon reaction testing. In one non-limiting example, the hydrocarbon reaction station 4 subjects a pre-loaded catalyst reactor tube 7 to hydrocarbon. Within the reaction station 4, a single pre-loaded catalyst reactor 7 is tested at any given time. Multiple catalyst reactors 7 are not tested within the hydrocarbon reaction station 4. Following hydrocarbon reaction testing, the gantry robot 8 moves reactor tubes 7 to the post-treatment station 5 for post-treatment testing. Multiple catalyst reactors 7 may be simultaneously post conditioned within the post treatment station 5. In one non-limiting example, the post treatment station 5 subjects one or more catalyst reactor tubes 7 to decoking. Following post-treatment testing, the gantry robot 8 moves reactor tubes 7 to the characterization station 6 for measurement of a catalyst property. Within the characterization station 6, a single pre-loaded catalyst reactor 7 is characterized at any given time. In one non-limiting example, the characterization station 6 measures BET of the catalyst reactor tube 7. Following catalyst characterization, the gantry robot 8 may move reactor tubes 7 back to the catalyst bank or storage station 1. Each of the stations 1, 2, 3, 4, 5, 6 may also be heated and controlled for temperature, pressure and/or gas flow rate.

The dashed lines within FIG. 1 signify communication between selected components to enable robotic automation via the gantry robot 8 coupled to the computer or programmable logic controller 10. The computer 10 may be used to not only control the movement of the gantry robot 8, but also for updating the testing queue for each station, automating catalyst selection, feed flow rates, pressure, temperature and other operating conditions. Valves, tape heaters, flow controllers, gas cylinders, tape heaters, furnace heaters, etc. are some of the other equipment in FIG. 1 that are not depicted for clarity reasons, but would be obvious to one skilled in the art.

Figure 2:
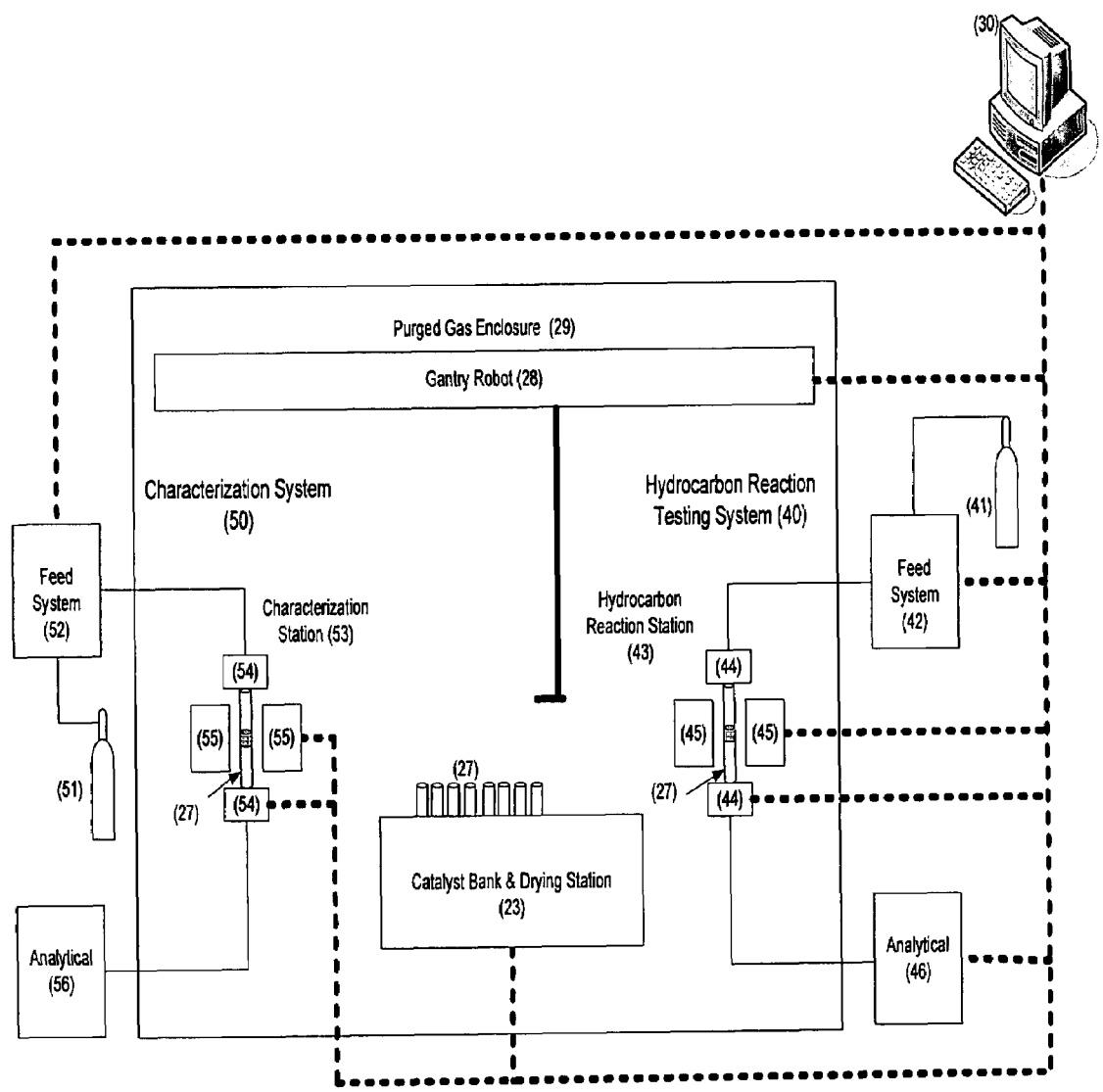
FIG. 2 depicts an alternative exemplary schematic of a process for testing catalysts via rapid serial experimentation including combining storage/pre-treatment, hydrocarbon reaction, and characterization stations.

FIG. 2 is an alternative exemplary process schematic of the method of the present invention for testing catalysts and catalyst systems via a plurality of station in which each station can accommodate a common reactor module in order to accomplish unattended, automated, rapid serial experimentation. FIG. 2 differs from FIG. 1 in having a combined catalyst reactor storage and preconditioning station 23 and does not include a post-conditioning station. FIG. 2 includes the following components: a catalyst bank/storage/drying/pre-conditioning station 23, a hydrocarbon reaction station 40, a characterization system 50, one or more pre-loaded catalyst reactor tubes 27, an overhead gantry robot 28, a purged gas enclosure 29, and a computer or programmable logic controller 30. The hydrocarbon reaction system 40 includes one or more gas cylinders 41, a hydrocarbon feed system 42, a hydrocarbon reaction station 43 (which includes a catalyst reactor tube holding mechanism 44 with top and bottom seats having polymeric "face" seals and a furnace heater 45 surrounding the catalyst reactor tube 27), and analytical instruments 46 for on-line reaction testing/measurement. On-line analytical instruments 46 may include a gas chromatograph, a mass spectrometer, an infrared detector or their combination. The characterization system 50 includes one or more gas cylinders 51, a gas feed system 52, a characterization station 53 (which includes a catalyst reactor tube holding mechanism 54 with top and bottom seats having polymeric "face" seals and a furnace heater 55 surrounding the catalyst reactor tube 27). Analytical 56 is for analyzing the product effluent of the characterization system.

Referring to FIG. 2, the gantry robot 28 moves the pre-loaded catalyst reactor tubes 27 between the storage/preconditioning station 23, the hydrocarbon reaction station 43 and the characterization station 53 within the confines of the purged gas enclosure 29, such that the catalyst reactor tubes 27 are moved within the process without exposure to air (anaerobic processing conditions). The storage/preconditioning station 23 for queuing catalysts includes at least one, and preferably multiple pre-loaded catalyst reactor tubes 27. Multiple catalyst reactors 27 may be simultaneously preconditioned within storage/preconditioning station 23. In one non-limiting example, the storage/preconditioning station 23 dries one or more catalyst reactors 27. The gantry robot 28 then moves a catalyst reactor tube 27 from the storage/preconditioning station 23 to the hydrocarbon reaction station 43 for hydrocarbon reaction testing. In one non-limiting example, the hydrocarbon reaction station 43 subjects a pre-loaded catalyst reactor tube 27 to methane. Within the reaction station 43, a single pre-loaded catalyst reactor 27 is tested at any given time. Multiple catalyst reactors 27 are not tested within the hydrocarbon reaction station 43.

Referring again to FIG. 2, following hydrocarbon reaction testing, the gantry robot 28 moves reactor tubes 27 to the characterization station 53 for measurement of a catalyst property. Within the characterization station 53, a single pre-loaded catalyst reactor 27 is characterized at any given time. In one non-limiting example, the characterization station 53 measures the surface area of the catalyst reactor tube 27. Following catalyst characterization, the gantry robot 28 may move reactor tubes 27 back to the storage/preconditioning station 23. Each of the stations 23, 43, 53 may also be heated and temperature controlled.

The dashed lines within FIG. 2 signify communication between selected components to enable robotic automation via the gantry robot 28 coupled to the computer or programmable logic controller 30. The computer 30 may be used to not only control the movement of the gantry robot 28, but also for holding and updating the testing queue for each station, automating catalyst selection, feed composition, feed flow rates, pressure, temperature and other operating conditions. Valves, flow controllers, liquid collection vessels, etc. are some of the other equipment in FIG. 2 that are not depicted for clarity reasons, but would be obvious to one skilled in the art.

The advantages of the disclosed method of using serial testing as a means to rapidly test catalysts and catalyst systems of the present invention include, inter alia, improved accuracy, reproducibility and quality of test data generated, increased testing throughput rate (decreasing testing time), providing for automated, unattended operation of the device, providing for the ability to program a variety of sequences and settings, providing for the combination of a variety of processes (pre-treatment, HC reaction testing, post-treatment, aging, and characterization), and providing for higher temperature operation. In addition, under the rapid serial approach of the present invention, the researcher takes advantage of the different time scales of the operations (pretreatment, HC reaction, post-treatment, and characterization) without adversely impacting throughput. More specifically in terms of increased testing throughput rate, the method of pretreatment of catalyst packed reactors in bulk enables reduced time in the reactor because the pretreatment step is already completed before the next serial test such as hydrocarbon testing, thereby increasing the rate of throughput. More specifically in terms of providing for the ability to program a variety of sequences and settings, the disclosed method of testing catalysts and catalyst systems via rapid serial experimentation provides for the ability to conduct pretreatment, hydrocarbon testing, characterization, aging and post-treatment in any specified order, including reproducing several steps. More specifically in terms of providing for automated unattended operation of the device, the disclosed method of testing catalysts and catalyst systems via rapid serial experimentation provides for the development of a queue for each station (HC testing, aging etc.) in a manner in which continuous, unattended operation is enabled such that down time is minimized and throughput is optimized. The disclosed method of using serial testing as a means to rapidly test catalysts and catalyst systems finds application in laboratory test environments, and in particular in high throughput testing environments.

Applicants have attempted to disclose all embodiments and applications of the disclosed subject matter that could be reasonably foreseen. However, there may be unforeseeable, insubstantial modifications that remain as equivalents. While the present invention has been described in conjunction with specific, exemplary embodiments thereof, it is evident that many alterations, modifications, and variations will be apparent to those skilled in the art in light of the foregoing description without departing from the spirit or scope of the present disclosure. Accordingly, the present disclosure is intended to embrace all such alterations, modifications, and variations of the above detailed description.

The following examples illustrate the present invention and the advantages thereto without limiting the scope thereof.

EXAMPLES

Example 1

A storage station or tray of pre-calcined catalyst packed tubular reactors (0.25 g each) was placed in the ante-chamber of a glove box. The ante-chamber was evacuated then nitrogen purged to 4 inches of water (gauge). The tray was then transferred to a heating block within the inert atmosphere of the glove box. The heating block already contained several trays currently in use for reaction testing and de-coking. Twenty-five catalyst packed reactors, situated in the trays in the heating block, had come to a steady-state temperature of 120° C. Each reactor within the heated tray were also continuously exposed to an inert purge to dry each catalyst for sufficient time so that each catalyst packed reactor was considered appropriately pre-treated and available for hydrocarbon testing. Automated robots selected a reactor tube from the pre-loaded tray and transferred it into the hydrocarbon assembly for testing. A furnace at 400° C., consisting of two sides, was then actuated (robotically) to enclose the catalyst and heat at 5° C./min to 800° C. The catalyst packed reactor was held for ~90 minutes then forced by fan to cool to 400° C. in 20 min. Simultaneously, a spent reactor of catalyst was transferred back to the reactor tray. It was then transferred to a coke characterization assembly. Similar to the hydrocarbon testing apparatus, a furnace, consisting of two parts, was actuated (robotically) to enclose the reactor of coked (spent) catalyst. The characterization feed header was then mixed to contain 1% oxygen in He. A temperature programmed oxidation (TPO) follows in order to determine the weight percent coke on catalyst and its distribution versus combustion temperature. The catalyst packed reactor was heated from 200° C. to 800° C. at 5° C./min. As each test was completed, a new catalyst reactor was selected automatically by the robot in series. The total test time was less than 3 hours for the 1 cycle of the tray of reactors.

| | |
|---|---|
| Pretreatment drying time | 2.5 hrs. |
| Hydrocarbon testing time (and cool down) | 3.0 hrs. |
| Temperature Programmed Oxidation | ~2 hrs. |
| Total time to compete an experiment for one reactor | ~3 hrs. |

The total time for one cycle of pre-treatment, HC reaction and characterization was determined by the longest time of any one step.

Example 2

Comparative

A reactor is packed with 0.25 g of catalyst. The reactor was manually loaded into a conventional 3 zone furnace assembly (required about 0.5 hr). It was pressure tested and then heated from 30° C. to 120° C. at 1° C./min and held for 1 hour to enable drying (total time of 2.5 hours). The catalyst packed reactor was then heated to 800° C. at 5° C./min. Hydrocarbon gas was then fed and allowed to react for approximately 1 hour. Total time for reaction was approximately 3.3 hours. Because of the mass of the traditional furnace and without fans, cool down required about 2 hours. At the same time, a sample of spent catalyst (different) was loaded on to a set-up to complete temperature programmed oxidation from 25° C. at 5° C./min to 800° C. Because the reactor had to be unloaded, and a TGA (Thermogravametric Analysis Instrument) pan loaded, 0.5 hrs was required to load the instrument. In addition, without an inert atmosphere, the oxidation had to be begun at 25° C. instead of 200° C., thus requiring overall time of 3 hours.

| | |
|---|---|
| Pretreatment drying time & reactor loading | 3.0 hrs. |
| Hydrocarbon testing time | 3.3 hrs. |
| Cool down time | 2.0 hrs. |
| Temperature Programmed Oxidation | 3.0 hrs. |

Overall, 1 cycle for the process required 8 hours compared to 3 hours for Example 1.

Example 3

The method of example 1 whereby the process flow was controlled via differential pressure across a critical orifice or by use of an automated variable orifice, such as a valve.

Example 4

The method of Example 1 by which a polymeric or grafitic materials was used to provided a seal between the tubular reactors and the supply/effluent line in any of the pretreatment, reaction, post-treatment or characterization stations.

Example 5

The method of Example 1 by which fuzzy logic was coupled with feed analysis to determine start time in Example 1.

Example 6

The method of Example 1 by which a protocol was defined to de-coke each sample after each reaction.

Example 7

The method of Example 1 by which a protocol was defined to alternate reaction/de-coking for a number of times for each sample, and by which the WHSV was varied to determine the kinetics of reaction for a single sample.

Example 8

The method of Example 1 by which a protocol was defined to only do reaction testing or de-coking.

Example 9

The method of Example 1 by which temperature was programmed with ramp rates and hold times for de-coking (temperature programmed oxidation).

Example 10

The method of Example 1 by which any number of reactions, pre-treatments, post-treatments and characterizations were combined to operate in a serial methodology.

Example 11

The method of Example 1 by which higher temperatures of operation were achieved in a high-throughput manner (via materials of construction).

Example 12

The method of Example 1 by which multiple cycles of hydrocarbon reaction, de-coking and characterization were realized.

Example 13

The method of Example 1 by which reactor tubes containing catalysts were dried in bulk (pretreatment) in order to minimize or reduce reaction testing time.

Example 14

The method of Example 1 by which robots were programmed to provide transport for reactor tubes between a pretreatment drying station, a hydrocarbon reaction station and de-coking characterization station in order to enable unattended, round-the-clock operation.

Example 15

The method of Example 1 by which valves were programmed to set a specification of a mixture of hydrocarbon feeds, conduct a feed analysis before reaction, start the feed to the reactor containing catalysts and stop according to defined, programmed recipes.

Example 16

The method of Example 1 by which the furnace for hydrocarbon testing and de-coking was automated to meet specified set-points, ramp rates and hold times in order test catalyst in a more efficient and exact manner.

Example 17

The method of Example 1 by which the furnace for hydrocarbon testing was robotically controlled to open and close robotically on a schedule as determined by computer in order to surround a catalyst packed reactor.

Example 18

The method of Example 1 by which fans were used to enable fast cool down of the furnace for any station.

Example 19

The method of Example 1 by which a mass spectrometer, gas chromatographs or infrared cells were used to measure a property of the catalyst or one or more of its subsequent products from testing or characterization.

What is claimed is:

1. A method of testing catalysts and catalyst systems via a plurality of stations, in which each station can accommodate a common reactor module in order to accomplish unattended, automated, rapid serial experimentation comprising the following steps:
    providing within one or more purged chambers a storage station of pre-loaded catalyst reactors, a hydrocarbon reaction station, a post-treatment station in series with said hydrocarbon reaction station, and a robotic means for moving catalyst reactors within said one or more purged chambers,
    moving with said robotic means a pre-loaded catalyst reactor from said storage station to said hydrocarbon reaction station,
    reacting said pre-loaded catalyst reactor with a hydrocarbon reactant in said hydrocarbon reaction station under controlled time, temperature, flow rate and pressure conditions,
    moving with said robotic means said pre-loaded catalyst reactor from said hydrocarbon reaction station to said post-treatment station,
    post-treating said pre-loaded catalyst reactor with a treatment gas in said post-treatment station under controlled time, temperature, flow rate and pressure conditions,
    moving with said robotic means said pre-loaded catalyst reactor from said post-treatment station to said storage station, and repeating the foregoing steps such that reacting and post-treating steps occur simultaneously for two different pre-loaded catalyst reactors.

2. The method of claim 1 in which said common reactor module is a pre-loaded catalyst reactor or an array of pre-loaded catalyst reactors.

3. The method of claim 2 wherein said post-treating step is performed on said common reactor module in bulk to enable faster cycle times in said hydrocarbon reaction station.

4. The method of claim 1 wherein said pre-loaded catalyst reactors are loaded with a catalyst selected from the group consisting of zeolites, mixed metal oxides, metal sulfides, metal nitrides, metal carbides, supported metals and combinations thereof.

5. The method of claim 1 in which said hydrocarbon reaction station and said post-treatment station are contained within one purged chamber.

6. The method of claim 1 wherein said hydrocarbon reactant is selected from the group consisting of methane, higher alkanes, olefins, aromatics, alcohols, ethers, oxygenates, carbon containing compounds, hydrogen containing compounds and oxygen containing compounds.

7. The method of claim 1 wherein said post-treating step is selected from the group consisting of decoking, drying, passivation, oxidation, reduction, carburization, sulfidation, nitridation, and phosphoridation.

8. The method of claim 1 further comprising the steps of:
providing a catalyst aging station in series with said hydrocarbon reaction station and said post-treatment station,
moving with said robotic means said pre-loaded catalyst reactor from one of said storage station, hydrocarbon reactant station, and post-treatment station to said catalyst aging station, and
subjecting said pre-loaded catalyst reactor in said catalyst aging station to thermal treatment, hydrothermal treatment, reduction, oxidation, carburization processes or combinations thereof.

9. The method of claim 1 further comprising the steps of:
providing a catalyst characterization station in series with said hydrocarbon reaction station and said post-treatment station,
moving with said robotic means said pre-loaded catalyst reactor from one of said storage station, hydrocarbon reactant station, and post-treatment station to said catalyst characterization station, and
subjecting said pre-loaded catalyst reactor in said catalyst characterization station to gas chromatography, mass spectrometry, infrared spectroscopy, chemisorption, acidity testing, adsorption, desorption, BET analysis, BJH analysis, surface area, pore volume, XRD, XRF, ICP, temperature programmed oxidation, temperature programmed reaction and temperature programmed reduction.

10. The method of claim 9 wherein said programmable logic controller or computer collects, analyzes and reports catalyst property data from said catalyst characterization station.

11. The method of claim 1 wherein said robotic means is controlled by a programmable logic controller or computer.

12. The method of claim 11 wherein said programmable logic controller or computer further controls station temperatures, test times, gas flow rates, and pressures.

13. The method of claim 1 wherein said programmable logic controller or computer collects and stores a queue of said pre-loaded catalyst reactors to be moved between said storage station, said hydrocarbon reaction station and said post-treatment station to optimize utilization of each station.

14. The method of claim 1 wherein said purged chamber is purged with nitrogen, hydrogen, helium, argon, or mixtures thereof.

15. A method of testing catalysts and catalyst systems via a plurality of stations, in which each station can accommodate a common reactor module in order to accomplish unattended, automated, rapid serial experimentation comprising the following steps:
providing within one or more purged chambers a storage station of pre-loaded catalyst reactors, a pre-treatment station, a hydrocarbon reaction station in series with said pre-treatment station, and a robotic means for moving catalyst reactors within said one or more purged chambers,
moving with said robotic means a pre-loaded catalyst reactor from said storage station to said pre-treatment station,
pre-treating said pre-loaded catalyst reactor with a treatment gas in said pre-treatment station under controlled time, temperature, flow rate and pressure conditions,
moving with said robotic means said pre-loaded catalyst reactor from said pre-treatment station to said hydrocarbon reaction station,
reacting said pre-loaded catalyst reactor with a hydrocarbon reactant in said hydrocarbon reaction station under controlled time, temperature, flow rate and pressure conditions,
moving with said robotic means said pre-loaded catalyst reactor from said hydrocarbon reaction station to said storage station, and
repeating the foregoing steps such that said pre-treating and reacting steps occur simultaneously for two different pre-loaded catalyst reactors.

16. The method of claim 15 in which said common reactor module is a pre-loaded catalyst reactor or an array of pre-loaded catalyst reactors.

17. The method of claim 16 wherein said pre-treating step is performed on said common reactor module in bulk to enable faster cycle times in said hydrocarbon reaction station.

18. The method of claim 15 wherein said pre-loaded catalyst reactors are loaded with a catalyst selected from the group consisting of zeolites, mixed metal oxides, metal sulfides, metal nitrides, metal carbides, supported metals and combinations thereof.

19. The method of claim 15 in which said hydrocarbon reaction station and said pre-treatment station are contained within one purged chamber.

20. The method of claim 15 wherein said pre-treating step is selected from the group consisting of decoking, drying, passivation, oxidation, reduction, carburization, sulfidation, nitridation, and phosphoridation.

21. The method of claim 15 wherein said hydrocarbon reactant is selected from the group consisting of methane, higher alkanes, olefins, aromatics, alcohols, ethers, oxygenates, carbon containing compounds, hydrogen containing compounds and oxygen containing compounds.

22. The method of claim 15 further comprising the steps of:
providing a catalyst aging station in series with said pre-treatment station and said hydrocarbon reaction station,
moving with said robotic means said pre-loaded catalyst reactor from one of said storage station, hydrocarbon reactant station, and pre-treatment station to said catalyst aging station, and
subjecting said pre-loaded catalyst reactor in said catalyst aging station to thermal treatment, hydrothermal treatment, reduction, oxidation, carburization processes or combinations thereof.

23. The method of claim 15 further comprising the steps of:
providing a catalyst characterization station in series with said hydrocarbon reaction station and said pre-treatment station,
moving with said robotic means said pre-loaded catalyst reactor from one of said storage station, hydrocarbon reactant station, and pre-treatment station to said catalyst characterization station, and
subjecting said pre-loaded catalyst reactor in said catalyst characterization station to gas chromatography, mass spectrometry, infrared spectroscopy, chemisorption, acidity testing, adsorption, desorption, BET analysis, BJH analysis, surface area, pore volume, XRD, XRF, or ICP.

24. The method of claim 23 wherein said programmable logic controller or computer collects, analyzes and reports catalyst property data from said catalyst characterization station.

25. The method of claim 15 wherein said robotic means is controlled by a programmable logic controller or computer.

26. The method of claim 25 wherein said programmable logic controller or computer further controls station temperatures, test times, gas flow rates, and pressures.

27. The method of claim 15 wherein said programmable logic controller or computer collects and stores a queue of said pre-loaded catalyst reactors to be moved between said storage station, said hydrocarbon reaction station and said pre-treatment station to optimize utilization of each station.

28. The method of claim 15 wherein said purged chamber is purged with nitrogen, hydrogen, helium, argon, or mixtures thereof.

29. A method of testing catalysts and catalyst systems via a plurality of stations, in which each station can accommodate a common reactor module in order to accomplish unattended, automated, rapid serial experimentation comprising the following steps:
providing within one or more purged chambers a storage station of pre-loaded catalyst reactors, a pre-treatment station, a hydrocarbon reaction station in series with said pre-treatment station, a post-treatment station in series with said hydrocarbon reaction station, and a robotic means for moving catalyst reactors within said one or more purged chambers,
moving with said robotic means a pre-loaded catalyst reactor from said storage station to said pre-treatment station,
pre-treating said pre-loaded catalyst reactor with a treatment gas in said pre-treatment station under controlled time, temperature, flow rate and pressure conditions,
moving with said robotic means said pre-loaded catalyst reactor from said pre-treatment station to said hydrocarbon reaction station,
reacting said pre-loaded catalyst reactor with a hydrocarbon reactant in said hydrocarbon reaction station under controlled time, temperature, flow rate and pressure conditions,
moving with said robotic means said pre-loaded catalyst reactor from said hydrocarbon reaction station to said post-treatment station,
post-treating said pre-loaded catalyst reactor with a treatment gas in said post-treatment station under controlled time, temperature, flow rate and pressure conditions,
moving with said robotic means said pre-loaded catalyst reactor from said post-treatment station to said storage station, and
repeating the foregoing steps such that said pre-treating, reacting and post-treating steps occur simultaneously for two different pre-loaded catalyst reactors.

30. The method of claim 29 in which said common reactor module is a pre-loaded catalyst reactor or an array of pre-loaded catalyst reactors.

31. The method of claim 30 wherein said pre-treating step is performed on said common reactor module in bulk to enable faster cycle times in said hydrocarbon reaction station.

32. The method of claim 31 wherein said post-treating step is performed on said common reactor module in bulk to enable faster cycle times in said hydrocarbon reaction station.

33. The method of claim 29 wherein said pre-loaded catalyst reactors are loaded with a catalyst selected from the group consisting of zeolites, mixed metal oxides, metal sulfides, metal nitrides, metal carbides, supported metals and combinations thereof.

34. The method of claim 29 in which said pre-treatment station, said hydrocarbon reaction station and said post-treatment station are contained within one purged chamber.

35. The method of claim 29 wherein said pre-treating step is selected from the group consisting of decoking, drying, passivation, oxidation, reduction, carburization, sulfidation, nitridation, and phosphoridation.

36. The method of claim 29 wherein said hydrocarbon reactant is selected from the group consisting of methane, higher alkanes, olefins, aromatics, alcohols, ethers, oxygenates, carbon containing compounds, hydrogen containing compounds and oxygen containing compounds.

37. The method of claim 29 wherein said post-treating step is selected from the group consisting of decoking, drying, passivation, oxidation, reduction, carburization, sulfidation, nitridation, and phosphoridation.

38. The method of claim 29 further comprising the steps of:
providing a catalyst aging station in series with said pre-treatment station, said hydrocarbon reaction station, and said post-treatment station,
moving with said robotic means said pre-loaded catalyst reactor from one of said storage station, hydrocarbon reactant station, pre-treatment station and post-treatment station to said catalyst aging station, and
subjecting said pre-loaded catalyst reactor in said catalyst aging station to thermal treatment, hydrothermal treatment, reduction, oxidation, carburization processes or combinations thereof.

39. The method of claim 29 further comprising the steps of:
providing a catalyst characterization station in series with said pre-treatment station, said hydrocarbon reaction station and said post-treatment station,
moving with said robotic means said pre-loaded catalyst reactor from one of said storage station, post-treatment station, hydrocarbon reactant station, and pre-treatment station to said catalyst characterization station, and
subjecting said pre-loaded catalyst reactor in said catalyst characterization station to gas chromatography, mass spectrometry, infrared spectroscopy, chemisorption, acidity testing, adsorption, desorption, BET analysis, BJH analysis, surface area, pore volume, XRD, XRF, or ICP.

40. The method of claim 39 wherein said programmable logic controller or computer collects, analyzes and reports catalyst property data from said catalyst characterization station.

41. The method of claim 29 wherein said robotic means is controlled by a programmable logic controller or computer.

42. The method of claim 41 wherein said programmable logic controller or computer further controls station temperatures, test times, gas flow rates, and pressures.

43. The method of claim 29 wherein said programmable logic controller or computer collects and stores a queue of said pre-loaded catalyst reactors to be moved between said storage station, said pre-treatment station, said hydrocarbon reaction station and said post-treatment station in order to optimize utilization of each station.

44. The method of claim 29 wherein said purged chamber is purged with nitrogen, hydrogen, helium, argon, or mixtures thereof.

* * * * *